May 21, 1963 P. ECKE Plant Pat. 2,259
POINSETTIA PLANT
Filed Oct. 19, 1961
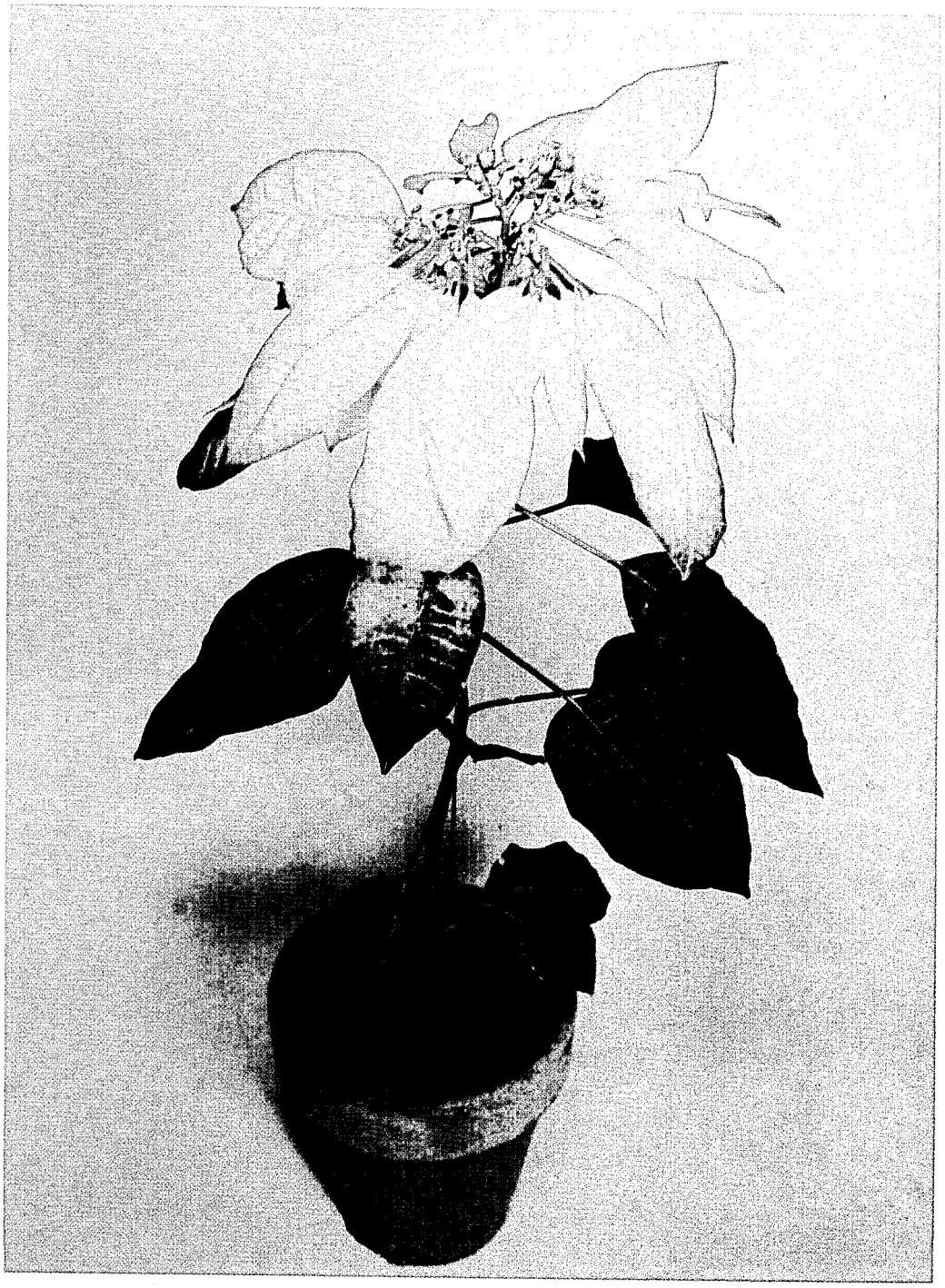
INVENTOR
Paul Ecke
by Wm. S. Graham
Attorney United States Patent Office Plant Pat. 2,259
Patented May 21, 1963

2,259
POINSETTIA PLANT

Paul Ecke, P.O. Box 488, Encinitas, Calif.

Filed Oct. 19, 1961, Ser. No. 146,387
1 Claim. (Cl. 47—60)

The subject of the present invention or discovery is a new and distinct variety of poinsettia plant (*Euphorbia pulcherrima*) originating as a cultivated sport.

Broadly, this new variety of poinsettia plant is distinguishable from its parent plant, as well as from other known varieties, mainly by its early blooming characteristic and the distinctive coloration of the foliage leaves which are more nearly adjacent to the bract involucre.

The accompanying illustration forming a part of this application graphically shows this new variety in color at substantially full maturity or optimum, the illustration being a perspective view taken from an angle above the plant and therefore illustrating the bracts and foliage leaves substantially as a full face view, as well as the characteristic coloring of the foliage leaves, which is a differentiating feature of this new variety.

The colors referred to herein correspond approximately with those shown in "Dictionary of Color" by Maerz & Paul (first edition, 1930), and identified by the common color names and by the plate of said color standard, as recapitulated in tabular form herein.

The following description more fully sets forth the characteristics of this new variety.

*Parentage*

This new variety was originated, discovered and cultivated by me in a cultivated area of the glass house at my experimental and growing gardens at Encinitas, California, by cuttings. It originated as a cultivated sport of poinsettia plant of the variety commonly called "Gloria," which is not patented but has been known in the trade by that name for many years though it is a variety which has acquired its greatest use and popularity in Europe, and not extensively in the United States up to this time.

*Propagation*

This new variety of poinsettia plant has been asexually reproduced by cuttings and has been cultivated by me in my said glass house, and successive reproductions thereof have remained true to type and it has shown its herein described qualities and characteristics to be permanently fixed. In asexually reproducing this new variety, I found it satisfactory and efficient to cut pieces of stalk of soft wood substantially six inches in length in or about the months of June, July and August, embedding one end of such cuttings in beds of sand in my glass house. After three or four weeks, the cuttings are well rooted and may be transferred to individual pots. My experience has been that the optimum temperature for propagation and growing under glass is of the order of 62 to 65 degrees F. night temperature, the daytime temperature being warmer, such as 70 to 75 degrees F., and subject to the varying conditions of light, heat, thickness of glass, cultivation, character of soil, fertilizer, and pruning or pinching.

*Habits of Growth*

This new variety of poinsettia plant develops its growth somewhat more rapidly than the normal average growth of poinsettia plants and will mature to optimum from about November 20th to December 10th, and produces the optimum of its bract involucre in the period from November 25th to about December 10th, which is approximately three weeks earlier than the usual well-known varieties of poinsettia plants. This new variety is hardy and healthy in growth, and its rate of growth may be characterized as somewhat faster than medium or average. This new variety seems to have an unusual resistance to disease and other detrimental factors and influences.

More particularly, this new variety is unusually resistant to a steam rot disease condition which is usually recognized as being caused by a root fungus designated rhizoctonia, and is also unusually resistant to a root rot condition caused by a fungus thielaviopsis, the detrimental factors of which are principally evidenced by leaf-drop of the foliage prior to complete maturity of the bract involucre and inflorescence. This resistance to disease and detrimental factors has been observed in this new variety when it has been grown side by side with other existing known varieties in the same field or in the same greenhouse condition, and the comparison of the new variety with known varieties has been observed over several years. These stated advantages of this new variety were established by observation of conditions present under usual and normal southern California field culture conditions in which night-time temperatures in winter frequently go down into the lower forties (F.). In plants grown in the greenhouse the temperature is maintained substantially uniformly around sixty to sixty-five degrees (F.), and the same conditions would not be so readily observable as under field grown conditions and comparisons.

*Structure*

This new variety has a well-developed spread of root structure. The peduncle or main stalk is of a medium green color and of usual medium strength, usually growing upwardly as a single stalk rather than spreading or having side shoots. Its normal average height is about 4 feet. The internode space between foliage leaves is quite uniform and regular. At the top or axial end of the peduncle, a node is formed from which grow several irregularly diverging pale yellow-tinted green bract-bearing branches or stem-like spurs, which bear the inflorescence and bract involucre. By reason of this spreading of the bract branches or spurs, the bracts themselves are spread irregularly from a center rather than radiating closely and uniformly from a single center, and the inflorescence on the diverging spurs is also thereby spread rather than concentrated at a single center.

*Bracts*

The bract involucre may be termed conventional in the sense that there is no characteristic substantial difference from the bract involucre of the parent variety known as "Gloria." But since the popularity of the "Gloria" variety has up to this time been more pronounced in Europe than in the United States, it is believed proper that the bract involucre of the present new variety may be briefly described. The bracts and also the petioles thereof are of a vivid pink-tinted rich red color which is closely similar to, but not quite so brilliant as, the colorations of bracts of the variety of poinsettia plant disclosed in my Plant Patent No. 1,779, dated December 9, 1958. Because of the diverging branches or spurs from which the bracts grow, the bracts are irregularly spaced from the center of the involucre, and, in addition, they have quite long petioles which further space them from a clustered center. The bracts vary widely in size, both in length and width, but they have a general uniformity of contour which is prolately ovate-acuminate, though there may be one or two bracts in an involucre which are oblate, which happens to be present in the specimen illustrated herein.

*Foliage Leaves*

The foliage leaves are arranged around the peduncle, the nodes thereof being quite uniformly spaced, and the petioles radiate in stepped staggered order from the peduncle. The petioles of the foliage leaves are reddish pink in color, and this same color extends with some modification into the dorsal vein of the foliage leaves, and to a lesser extent into the venation of the foliage leaves. The foliage leaves are of a generally rose-leaf acute ovate shape, without serrations at the edge, and are quite regularly veined in the herringbone manner. One of the predominant distinguishing characteristics of this new variety is the varying coloration of the foliage leaves. Those leaves, which are remotely spaced from the bract involucre are of a medium green color, similar to the foliage leaves of the parent plant "Gloria." A group of four to six foliage leaves which are relatively spaced next adjacent to the bracts have variations of color, varying from a dark green with a purplish tint for those leaves in that group which are more remote from the bracts; whereas, those leaves in that group which are more nearly adjacent to the bracts are of a much lighter shade of purple with a reddish tint, and those foliage leaves which are immediately and next adjacent to the bracts are variegated or splashed with areas simulating the rich pink-tinted red coloring of the bracts.

*Inflorescence*

The inflorescence grows in clusters upon the pale green branches or spurs heretofore described as branching irregularly and divergingly upwardly and expansively apart from the free axial end of the peduncle and centrally of the bract involucre. This inflorescence is also similar to the inflorescence of the "Gloria" variety. Upon the length of the spur branches grow the flower cyathium on short sub-acaulescent stems. As in a large number of varieties of poinsettia plants, the cyathium is of pale green color, small and not prominent, and the flower growing therefrom is orange yellow in color with a touch of crimson red center. Since the spurs diverge relatively, the inflorescence growing thereon is in relatively spaced clusters, spreading the flower clusters towards the bracts, which provides a very attractive unformalized appearance to the bract involucre as an entirety.

*Variations*

Different plants of this variety have an unusual similarity of adherence to characteristics and type herein described. However, there may be some variation in the characteristics of minor details, in comparison of plants growing in various localities, in different soils, and in different times of the year, varying temperatures, varying types of glass house, or out of doors.

*Color Tabulation*

The color designations according to the color plates of said "Dictionary of Color" are recapitulated in tabular form as follows:

| Part of plant | Non-Technical designation of color | Dictionary of color | | |
|---|---|---|---|---|
| | | Plate | Letter | Number |
| STRUCTURE | | | | |
| Peduncle, main stalk | Medium green | 24 | H | 1 |
| Bract-bearing spurs | Yellow-tinted green | 17 | J | 6 |
| BRACTS | | | | |
| Bracts | Pink-tinted rich red | 1 | L | 3 |
| Petioles of bracts | do | 1 | L | 3 |
| FOLIAGE LEAVES | | | | |
| 1. Remotely spaced from bracts. | Medium green | 24 | H | 1 |
| 2. Foliage leaves in the group of four to six next adjacent bracts: | | | | |
| (a) Those more remote from bracts (in this group). | Dark green with purple tint. | 24 | A | 12 |
| (b) Those more nearly adjacent to the bracts (in this group). | Light purple with reddish tint. | 44 | L | 8 |
| (c) Those immediately and next adjacent bracts (in this group). | Light purple variegated with splashed areas of pink-tinted red simulating color of bracts. | 43<br>1 | L<br>L | 8<br>3 |
| Petioles of foliage leaves | Reddish pink | 41 | L | 5 |
| Dorsal vein of foliage leaves | do | 41 | L | 5 |
| INFLORESCENCE | | | | |
| Cyathium | Pale green | 17 | I | 6 |
| Flower | Orange yellow | 10 | K | 6 |
| Center of flower | Crimson red | 41 | L | 4 |

Having described and illustrated my new variety of poinsettia plant, I claim:

A new and distinct variety of poinsettia plant substantially as illustrated and described, characterized by bracts of a brightness and vividly rich pink-tinted red color, its quality of early blooming, and more especially characterized by the variation of coloring of the foliage leaves, in that the foliage leaves more remotely removed from the bract involucre are of medium green color and the foliage leaves more nearly adjacent to the bract involucre, such as the group of four to six leaves spaced from the involucre, have a purple color which is of darker purple color in the foliage leaves of that group which are more remote from the bracts, and graduating to a lighter shade of purple in the foliage leaves in that group more nearly adjacent to the bracts, and the said last mentioned foliage leaves which are next adjacent to the bracts being irregularly splashed with color approximating the color of the bracts.

No references cited.